US011779293B2

(12) United States Patent
McCarthy et al.

(10) Patent No.: US 11,779,293 B2
(45) Date of Patent: Oct. 10, 2023

(54) SYSTEM AND METHOD FOR THERMAL LOAD PREDICTION OF PROPOSED IMAGING PROCEDURES FOR X-RAY TUBES

(71) Applicant: GE Precision Healthcare LLC, Wauwatosa, WI (US)

(72) Inventors: Thomas McCarthy, Paris (FR); Lionel Desponds, Saint-Rémy-lès-Chevreuse (FR)

(73) Assignee: GE Precision Healthcare LLC, Wauwatosa, WI (US)

(*) Notice: Subject to any disclaimer, the term of this patent is extended or adjusted under 35 U.S.C. 154(b) by 147 days.

(21) Appl. No.: 17/514,184

(22) Filed: Oct. 29, 2021

(65) Prior Publication Data
US 2023/0133721 A1    May 4, 2023

(51) Int. Cl.
*A61B 6/00*    (2006.01)

(52) U.S. Cl.
CPC ............. *A61B 6/487* (2013.01); *A61B 6/461* (2013.01); *A61B 6/544* (2013.01)

(58) Field of Classification Search
CPC .......... A61B 6/461; A61B 6/487; A61B 6/544
See application file for complete search history.

(56) References Cited

U.S. PATENT DOCUMENTS

| 4,991,189 | A | * | 2/1991 | Boomgaarden | ...... A61B 6/4021 378/19 |
| 5,497,410 | A | | 3/1996 | Behling | |
| 5,982,849 | A | * | 11/1999 | Bischof | .................... H05G 1/36 378/127 |
| 6,351,517 | B1 | * | 2/2002 | Guru | ....................... H05G 1/54 378/91 |

(Continued)

FOREIGN PATENT DOCUMENTS

| DE | 10255955 B3 | 8/2004 |
| DE | 102020210804 A1 * | 9/2021 |
| EP | 2903526 B1 | 9/2017 |

OTHER PUBLICATIONS

Translation of DE-102020210804 (Year: 2021).*

*Primary Examiner* — Dani Fox
*Assistant Examiner* — Soorena Kefayati
(74) *Attorney, Agent, or Firm* — Boyle Fredrickson, S.C.

(57) ABSTRACT

A system and method for the prediction of a thermal load for a proposed imaging procedure in view of the current thermal state for an imaging system employs a suitable software program/algorithm which determines a predicted or likely set of individual steps for a proposed imaging procedure to be performed. The system receives parameters for the particular imaging procedure to be performed and compares these parameters with information stored concerning prior performed imaging procedures to locate prior performed imaging procedures that have similar parameters to that for the proposed imaging procedure. The system utilizes the (Continued)

similar prior performed procedures as models of a likely set of imaging steps for the proposed procedure and estimates the heat generation produced by the models. The software program/algorithm can then determine if the entire proposed imaging procedure represented by the models can be successfully performed under the current thermal state for the imaging system.

18 Claims, 3 Drawing Sheets

(56) References Cited

U.S. PATENT DOCUMENTS

| | | | | |
|---|---|---|---|---|
| 7,885,384 B2* | 2/2011 | Mannar | ............ | A61B 6/586 |
| | | | | 378/207 |
| 2004/0151279 A1* | 8/2004 | Beck | ............ | A61B 6/465 |
| | | | | 378/98 |
| 2005/0206769 A1* | 9/2005 | Kump | ............ | G06F 1/3203 |
| | | | | 348/333.01 |
| 2005/0207534 A1* | 9/2005 | Petrick | ............ | G01T 1/2985 |
| | | | | 378/114 |
| 2012/0106709 A1* | 5/2012 | Hockersmith | ............ | H05G 1/36 |
| | | | | 378/130 |
| 2014/0233708 A1* | 8/2014 | Ishiyama | ............ | H05G 1/54 |
| | | | | 378/207 |
| 2014/0254748 A1* | 9/2014 | Funk | ............ | A61B 6/14 |
| | | | | 378/19 |
| 2015/0230766 A1* | 8/2015 | Wang | ............ | A61B 5/0035 |
| | | | | 600/411 |
| 2015/0312999 A1* | 10/2015 | Takahashi | ............ | A61B 6/0487 |
| | | | | 378/92 |
| 2017/0143214 A1* | 5/2017 | Garibotto | ............ | G01J 5/0025 |
| 2017/0188443 A1* | 6/2017 | Nakahara | ............ | A61B 6/40 |
| 2019/0090840 A1* | 3/2019 | Nagesh | ............ | A61B 6/035 |
| 2019/0304600 A1* | 10/2019 | Mogatadakala | ............ | A61B 6/40 |
| 2019/0320994 A1* | 10/2019 | Lemaitre | ............ | A61B 6/582 |
| 2019/0365338 A1* | 12/2019 | Haider | ............ | G16H 40/63 |
| 2020/0121274 A1* | 4/2020 | Hofmann | ............ | A61B 6/032 |
| 2020/0289851 A1* | 9/2020 | Dilmanian | ............ | A61N 5/1042 |
| 2021/0022690 A1* | 1/2021 | Matsuura | ............ | A61B 6/5205 |
| 2021/0251584 A1* | 8/2021 | Nae | ............ | A61B 6/0407 |

* cited by examiner

SYSTEM AND METHOD FOR THERMAL LOAD PREDICTION OF PROPOSED IMAGING PROCEDURES FOR X-RAY TUBES

FIELD OF THE DISCLOSURE

The present disclosure relates generally to X-ray imaging systems and methods, and more specifically to systems for determination of a thermal load prediction of proposed imaging procedures based on thermal modeling and simulation during the operation of imaging systems employing X-ray tubes.

BACKGROUND OF THE DISCLOSURE

X-ray imaging systems and devices include an X-ray source or tube that emits a collimated beam of X-rays to image an object/patient. In such systems, an X-ray detector is positioned with respect to the X-ray source so as to receive the X-rays that have passed through the object. The X-ray source and the X-ray detector may be immobile or can individually move or move in unison along a path that traverses the object during a scan. The detectors of many such systems typically output/produce electrical signals in response to the received X-rays.

In an imaging procedure, operation of the X-ray source creates a significant amount of heat through various sources, and primarily through the impacts of the X-rays generated from the cathode upon the anode target. As a result, the generated heat must be removed from the X-ray tube in order to prevent overheating and potential failure of the components of the X-ray tube.

To accomplish this, X-ray tubes include one or more flows of a cooling fluid directed around and/or through the X-ray tube to indirectly thermally contact the heat-generating components of the X-ray tube and transfer the generated heat to the cooling fluid, which is subsequently circulated through an external heat exchanger for removal of the heat prior to re-introduction of the cooling fluid back into contact with the X-ray tube. For example, a flow of cooling fluid can be directed through an X-ray tube casing disposed around and enclosing the X-ray tube insert. The cooling fluid directed through the casing thermally contacts the exterior of the X-ray tube insert to transfer heat from exterior of the X-ray tube insert to the cooling fluid, which is removed by an external heat exchanger and/or a separate flow of another cooling fluid passing through the casing.

However, regardless of the types of cooling flows utilized with a particular X-ray tube, the limited heat capacity of the X-ray tube is a problem for X-ray imaging systems. More specifically, on average the amount of heat generated by the operation of the X-ray tube can be significantly larger than the amount of heat that can be removed by the cooling fluid flows during the operational time for the X-ray tube. Therefore, the heat produced by the operation X-ray tube cannot be extracted fast enough by the cooling fluid flows such that a large amount of residual heat remains within the components of the X-ray tube after operation.

To accommodate for this heat generation and to protect the X-ray tube internal components from overheating beyond their operational thermal limits and becoming damaged, a number of prior art devices and processes have been developed to monitor the temperature of the X-ray tube and provide warnings regarding sensed temperature levels nearing the operational limits for the X-ray tube. While some devices introduced the use of temperature sensors located on the X-ray tube in order to obtain more accurate readings on the actual temperature level within the X-ray tube, other developed solutions utilize X-ray tube protection software and/or algorithms within the X-ray imaging systems. These algorithms usually model the heat transfer in parts of the X-ray tube where a direct measurement of the temperature is a technical challenge, such as for moving parts in a vacuum with high voltage applied to them, such as the target track on the anode target. The algorithms can estimate when the temperature within the X-ray tube is reaching predetermined limits for the temperature, such as a percentage of the maximum operational temperature for the X-ray tube. An indicator of this current temperature provided by the algorithm, such as on a display for the imaging system including the X-ray tube, can be an indication of the Heat Unit Available (HUA), often represented as a percentage of the maximum heat that can be accumulated within the X-ray tube.

With the tube protection software/algorithms, when the sensed/calculated temperature reaches a predetermined level the software/algorithm can provide an indication of the temperature condition represented by that level to the operator. For example, the algorithm can indicate that the temperature of the X-ray tube is approaching certain predetermined limits specified by the imaging system manufacturer, such as when HUA is below 20%, to warn the user about the current heat status for the X-ray tube. In addition, when the tube protection software/algorithm determines the X-ray tube is reaching 0% of HUA, the software/algorithm can operate to protect the X-ray tube by preventing any further imaging from being performed until the X-ray tube cools to a sufficient level of HUA. This process can be employed by the software/algorithm to estimate the heat generation for the next successive acquisition or step in an in-process imaging sequence. This estimation can then be compared with the current HUA calculated for the X-ray tube to see if the next step/acquisition can be performed without exceeding the HUA limits for the X-ray tube. Alternatively, the software/algorithm can warn or notify the user that the temperature has reached 0% HUA and that any further operation of the X-ray tube will void any product warranty on the X-ray tube.

In these situations, oftentimes it is the experience of the operator that determines whether to proceed with an on-going examination or start an imaging procedure, as the operator can estimate based on prior imaging procedures performed whether the imaging procedure can be safely performed and/or continued within the HUA indicated by the imaging system. The manufacturer of the device may also provide guidelines or recommendations on deciding whether to initiate a procedure based on the level of HUA, for example, such as ensuring that at least 50% is available prior to starting an intervention.

In any of these situations, the operation of the tube protection software/algorithm effectively limits and/or prevents any use of the imaging system to avoid overheating and damage to the X-ray tube. As a result, the significant drawback is that the prevention by the algorithm of the operation of the X-ray tube often results in significant periods of non-availability for the imaging system without any advance notice to the user, which can occur in the middle of an imaging sequence/procedure being performed by the imaging system.

One way that has been developed to mitigate the unexpected non-availability of the imaging system due to elevated temperatures of the X-ray tube is to increase the remaining capacity of the X-ray tube anode by applying an automatic derating to the operation of the X-ray tube, i.e., a reduction of the input power supplied to the X-ray tube when in operation. This derating is done just prior to the execution of a particular sequence, and results in a corresponding lowering of the image quality without control from the user. The reduction in input power is usually set to be small enough to avoid a sharp decrease in image quality but can still create the situation where an imaging system non-availability unexpectedly occurs based on temperature generation that interrupts the in-process imaging sequence/procedure.

In further attempts to limit any unexpected non-availability of the imaging system and/or avoid the interruption of any in-process imaging sequence, or unexpected derating of the operation of the X-ray tube, some additional prior art solutions utilize the increased computing capabilities of the tube protection software/algorithms to calculate thermal simulations in a rapid manner. In particular, progress in thermal modeling as well as increases in processing power enable modeling of heat transfer between multiple elements of an X-ray tube. As a result, current tube protection software/algorithms can analyze a proposed imaging procedure to determine if the heat generation estimated for the proposed procedure exceeds the current HUA for the imaging system, i.e., whether the heat generation exceeds the maximum operating temperature of any of the elements in the X-ray tube, and if so, what waiting time if any is required to reach the minimum HUA for performance of the proposed imaging procedure.

However, though able to be performed quickly by the tube protection software/algorithms, these heat generation estimations are limited to standardized or simplified steps for the proposed imaging procedure, and cannot take into account the particulars of the actual imaging procedure to be performed, including patient size and/or any required variations from the standardized steps utilized in the estimations.

Therefore, it is desirable to develop an improved system and method for providing an accurate prediction of whether the particular parameters of a proposed imaging procedure or examination can be completed to avoid unnecessary imaging procedure denials or extended wait times.

SUMMARY OF THE DISCLOSURE

According to one aspect of an exemplary embodiment of the disclosure, an improved system and method for the prediction of a thermal load for a proposed imaging procedure in view of the current HUA for an imaging system employs a suitable software program/algorithm which determines a predicted or likely set of individual steps for a proposed imaging procedure to be performed. The determination is made by the software program/algorithm first receiving parameters for the particular imaging procedure to be performed. The software/algorithm then compares these parameters with a database including information stored concerning prior performed imaging procedures or cases in order to locate prior performed imaging procedures that have similar parameters regarding the type of imaging procedure to be performed to that for the proposed imaging procedure. With the stored information for the prior performed procedure(s), the software program/algorithm utilizes the similar prior performed procedures as models of a likely set of procedural imaging steps for the proposed procedure that accurately predict or approximate what the proposed imaging procedure will be and estimates the heat generation to be produced by the proposed imaging procedure. The software program/algorithm can then determine if the proposed imaging procedure can be successfully performed under the current HUA conditions for the imaging system.

According to another aspect of an exemplary embodiment of the disclosure, the thermal prediction system can locate prior performed procedures that are used as models which approximate and/or predict the steps for the proposed imaging procedure in order to determine the individual steps performed in the prior performed procedures. The software/algorithm then can modify the predicted or likely steps in the prior performed procedures/models based on parameters particular to the current patient to compile a refined likely set of steps and/or operating parameters in the prior performed procedures/models as predicted to be performed in the proposed imaging procedure. Once complied, the modified prior performed procedures/models including the predicted set of steps for the proposed imaging procedure can be analyzed to determine the potential for the entirety of the proposed imaging procedure to be performed successfully within the current HUA limitations of the imaging system. If any one or more of the predicted or likely steps of the models for the proposed imaging procedure are determined to exceed the current HUA limitations and cause a derating or a protection, the software/algorithm can alert the operator to indicate a waiting time to achieve the required HUA limitations to successfully complete the proposed imaging procedure and/or propose alterations to the proposed imaging procedure in order to enable the proposed imaging procedure to be successfully completed. Some examples of the proposed alterations to the proposed imaging procedure that can be utilized include employing a reduced power level from the start of the case to avoid an unexpected derating during a more critical phase, or at least for part of the case, using a second X-ray tube instead of a first X-ray tube in case of a multi-tube system.

According to still another aspect of an exemplary embodiment of the disclosure, an X-ray imaging system includes an X-ray source configured to emit radiation beams towards the object, an X-ray detector movably aligned with the X-ray source to receive the radiation beams from the X-ray source and generate image data, a controller operably connected to the X-ray source and the X-ray detector to control the movement and operation of the X-ray source and X-ray detector, the controller configured to receive and process image data from the X-ray detector, a display operably connected to the controller for presenting information to a user, a user interface operably connected to the controller to enable user input to the controller, and a thermal prediction system including a processing unit, and an electronic storage device including data on a number of prior performed imaging procedures, wherein the processing unit for the thermal prediction system is configured to match proposed imaging procedure data with one or more prior performed cases to create one or more models for the proposed imaging procedure, and to perform a thermal prediction on the one or more models.

According to still another aspect of an exemplary embodiment of the present disclosure, a method for predicting the outcome for performing a complete proposed X-ray imaging procedure on an object includes the steps of providing an X-ray imaging system having a X-ray source configured to emit radiation beams towards the object, an X-ray detector movably aligned with the X-ray source to receive the radiation beams from the X-ray source and generate image data, a controller operably connected to the X-ray source and the X-ray detector to control the movement and operation of the X-ray source and X-ray detector, the controller configured to receive and process image data from the X-ray detector, a display operably connected to the controller for presenting information to a user, a user interface operably connected to the controller to enable user input to the controller, and a thermal prediction system including a processing unit, a number of optional sensing devices disposed on the X-ray source and configured to send thermal data to the thermal prediction system and an electronic storage device including data on a number of prior performed imaging procedures, providing proposed imaging procedure data to the thermal prediction system, matching the proposed imaging procedure data with one or more prior performed cases to create one or more models for the proposed imaging procedure; and performing a thermal prediction on the one or more models.

According to another exemplary aspect of the disclosure, a thermal prediction system for an X-ray imaging system includes a processing unit, a number of thermal sensing devices adapted to be disposed on an X-ray source for the X-ray imaging system, and configured to send thermal data to the processing unit and an electronic storage device including data on a number of prior performed imaging procedures, wherein the processing unit for the thermal prediction system is configured to match proposed imaging procedure data with one or more prior performed cases to create one or more models for the proposed imaging procedure, and to perform a thermal prediction on the one or more models.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments. As used herein, the terms "substantially," "generally," and "about" indicate conditions within reasonably achievable manufacturing and assembly tolerances, relative to ideal desired conditions suitable for achieving the functional purpose of a component or assembly. Also, as used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process.

Exemplary embodiments of the invention relate to an X-ray tube including an increased emitter area to accommodate larger emission currents in conjunction with microsecond X-ray intensity switching in the X-ray tube. An exemplary X-ray tube and a employing the exemplary X-ray tube are presented, though the invention is also applicable to computed tomography (CT) and other types of X-ray imaging systems.

Figure 1:
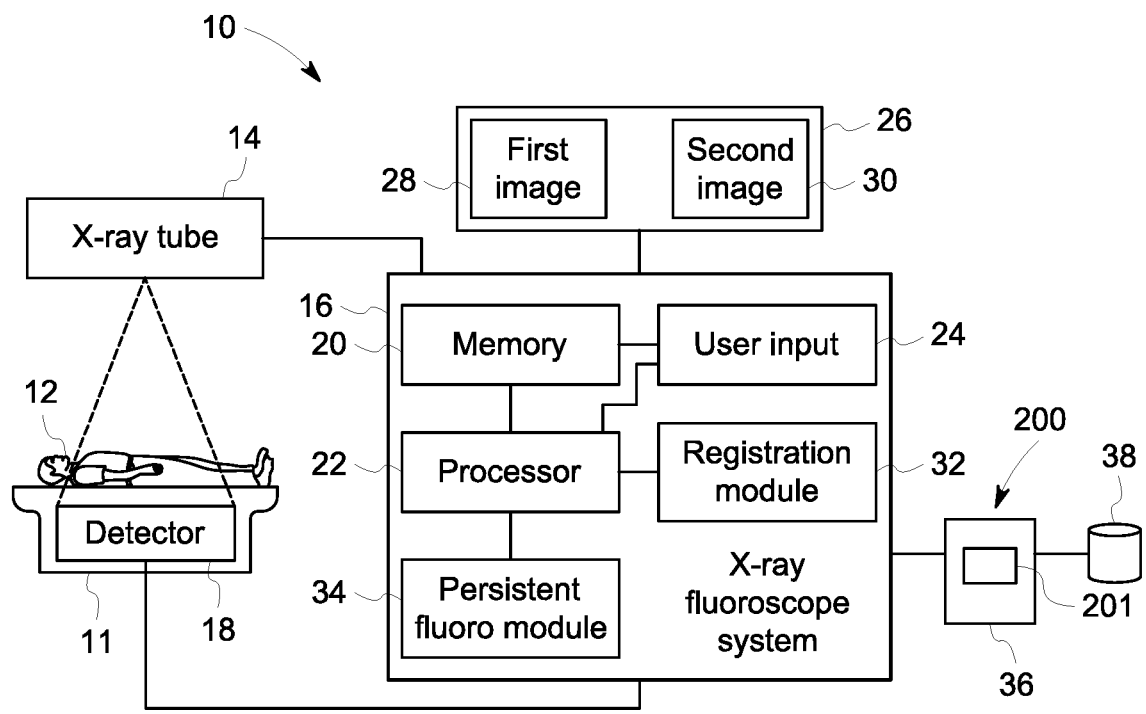
FIG. 1 is a schematic view of an imaging system for use with the thermal prediction system in accordance with an exemplary embodiment of the disclosure.

Referring now to FIG. 1, an x-ray fluoroscopic imaging system 10 (also referred to as a fluoroscope), such as that disclosed in U.S. Pat. No. 8,379,795, entitled Methods And Apparatus For Archiving X-Ray Fluoroscopy Images, the entirety of which is expressly incorporated herein by reference for all purposes, may be used to obtain real-time moving images of the internal structures of a patient 12. The x-ray fluoroscopic imaging system 10 includes a table 11 or bed for supporting the patient 12. An X-ray tube 14 or other generator is connected to an x-ray fluoroscopic processing sub-system 16. As shown, the x-ray tube 14 is positioned above the patient 12, but it should be understood that the x-ray tube 14 may be moved to other positions with respect to the patient 12. A detector 18 is positioned opposite the x-ray tube 14 with the patient 12 therebetween. The detector 18 may be any known detector capable of detecting x-ray radiation.

The x-ray fluoroscopic processing sub-system 16 includes at least a memory 20, a processor 22 and at least one user input 24, such as a keyboard, trackball, pointer, touch panel, and the like. To acquire an x-ray image, the x-ray fluoroscopic processing sub-system 16 causes the x-ray tube 14 to generate x-rays and the detector 18 detects x-rays that pass through the patient 12 and impinge on the detector 18. Fluoroscopy may be accomplished by activating the x-ray tube 14 continuously Or at predetermined intervals while the detector 18 detects corresponding emitted x-rays. One or more image(s) 28 and 30, for example, fluoroscopic x-ray images generated from the detected x-rays during a low dose scan may be displayed in real-time on a display 26 that may be configured to display a single image or more than one image at the same time, such as an image sequence. It should be noted that the images 28 and 30 acquired by x-ray fluoroscopic imaging system 10 may be acquired in any known manner. The images 28 and 30 are automatically stored in a mass electronic storage device or database 38 during image acquisition, which may be formed as a part of the system 10 or at an archival location separate from the system 10. It also should be noted that the display 26 may be configured to include different portions for viewing real-time images and for reviewing and selecting images for permanent storage, such as in a mass electronic storage device or database 38, for later review and/or processing.

The x-ray fluoroscopic processing subsystem 16 also may include a registration module 32, which may be a processor configured to process received image data to register the first and second images 28 and 30 with respect to each other. The x-ray fluoroscopic processing subsystem 16 also may include a persistent fluoro module 34 to control the real-time display of fluoro images or sequences, the automatic storing of the acquired fluoro images or sequences and other data regarding the images or sequences in mass storage 38, including imaging process steps, imaging process time for each step and for the overall imaging process, HUA data for the individual steps and for the overall imaging process, and individual patient identification data, including demographic, morphology and imaged anatomy data, and the operation of a user interface 24.

Figure 2:
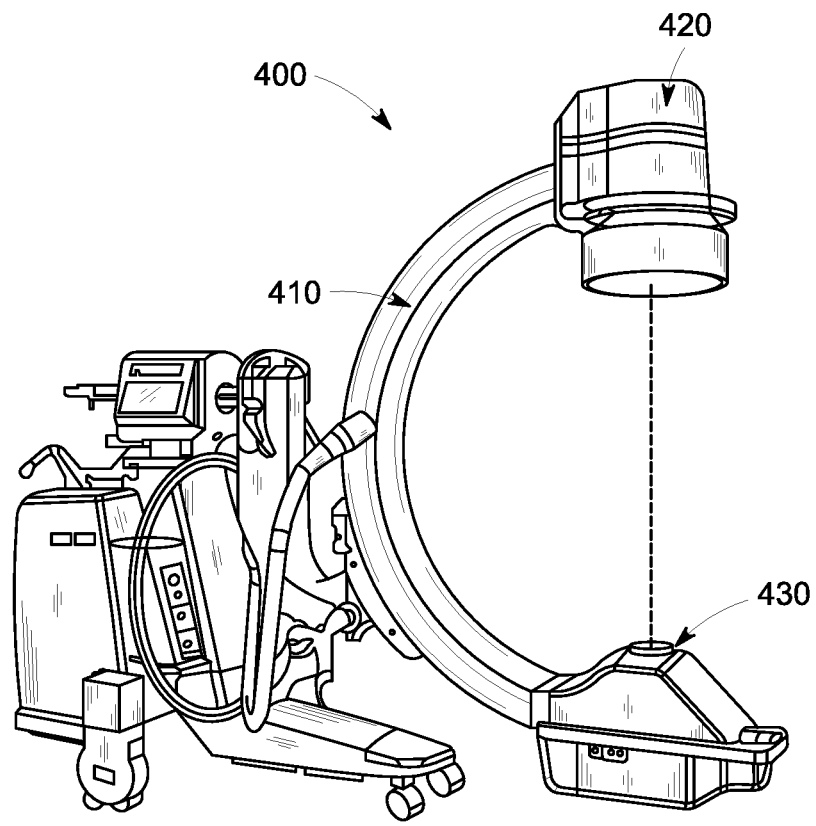
FIG. 2 is an isometric view an imaging system for use with the thermal prediction system in accordance with another embodiment of the disclosure.

The imaging system 10 may be implemented as a non-mobile (as shown in FIG. 1) or mobile imaging system as shown in FIG. 2. For example, FIG. 2 illustrates a mobile imaging system 400 that may be used in accordance with one embodiment and configured as a mobile fluoroscopic imaging system. The mobile imaging system 400 may include some or all of the imaging system 10 or a similar system. The mobile imaging system 400 includes a C-arm 410, an energy source 420 (e.g., an x-ray energy source), an image acquisition device 430 (e.g., a detector or camera) and a positioning surface (e.g., a patient positioning table, not shown). Optionally, the C-arm 410 may be, for example, an L-arm, an O-arm, a C-gantry, and/or other positioning element. Also, the imaging system 400 may be implemented as a stand-alone or wall mounted unit. In operation, an object may be positioned on the positioning surface. Image data related to the object may be obtained at the image acquisition device 430 after energy from the energy source 420 has irradiated the object. Thus, fluoroscopic images may be acquired of patient or a region of interest of the patient.

The fluoro images can additionally applied as an input to a computer 36 operably connected to but separate from the system 10, which stores the images in an electronic mass storage device or database 38 for further processing or viewing.

Figure 3:
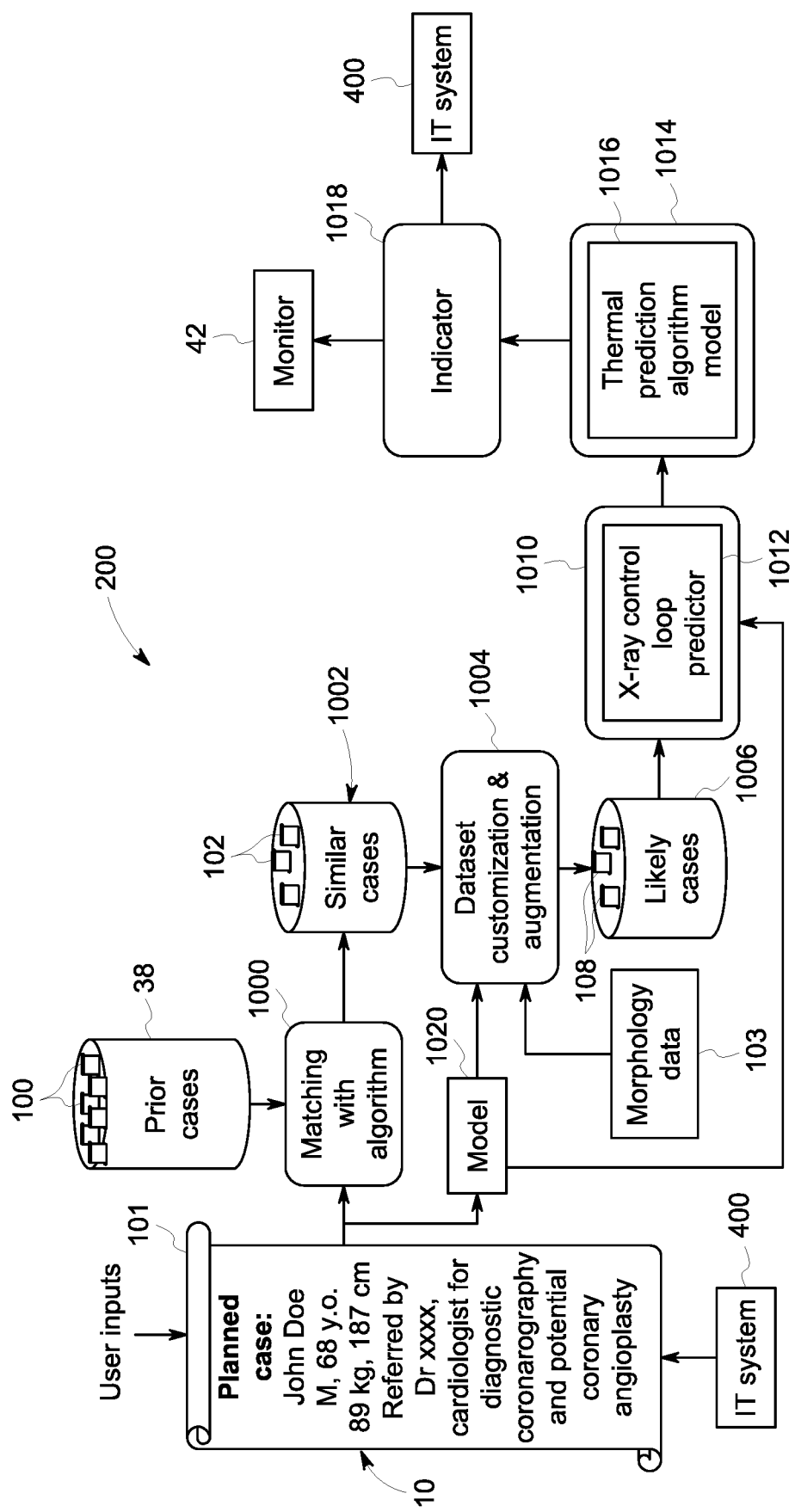
FIG. 3 is a flowchart of the operation of the thermal prediction system in accordance with an exemplary embodiment of the disclosure.

Referring now to FIGS. 1-3, the system 10 includes a thermal prediction system 200 formed with a processing unit 201 electrically operably connected to the processing unit/computer 36 or formed as a part of the processing unit/computer 36, or as a part of the imaging system 10 in other embodiments. The thermal prediction system 200 may optionally include a number of sensing devices/sensors 202 disposed on the X-ray source 14 to supply thermal data in any suitable manner, e.g., via wires or wirelessly, to the thermal prediction system 200 for determination of HUA for the X-ray source 14. In certain exemplary embodiments, the sensing devices 202 can be one or more of: coolant temperature sensors at the input and output of the X-ray source/tube 14, a coolant flow sensor which can enable the system 200 to adapt the thermal prediction model if the interruptions in coolant flow are detected, an ambient air temperature sensor, a sensor for measuring the rotational speed of the anode/target and/or a sensing device to provide the power consumption of the X-ray tube 14, each to provide data inputs to the thermal prediction system 200.

The thermal prediction system 200 is electrically connected to the mass storage device 38, which can be located on the imaging system 10 or on a remote computer system 400 and also includes stored data files relating to a number of prior performed imaging procedures or cases 100. The data recorded and/or stored in the storage device 38 for each prior performed case 100 can include information relating to the type of acquisition performed, and the complexity of the entire acquisition, including the actual steps utilized in the prior performed case 100, such as the dose setting, duration and number of each imaging step and/or sequence, as well as the number and durations of the pauses in-between the imaging sequences. Additional information stored regarding the prior performed cases 100 can include various patient demographics, such as the size of the patient (large, small, etc.), and patient age, among others.

In block 1000, the system 200 can utilize input information 101 provided to the thermal prediction system 200 by the operator concerning the current patient and the proposed imaging procedure for comparison with the data in storage device 38. Because every case is different and the different factors cannot be completely predicted based on prior data, the first step is to establish a set of likely steps for the proposed imaging procedure. The input, i.e., selecting the type of case to be performed, can be made by the operator at the start of the case or documented in advance in the hospital scheduling software/remote computer system 400, e.g., a hospital scheduling system, operably connected to the imaging system 10 and/or thermal prediction system 200.

In this comparison, the thermal prediction system 200 attempts to match the entered parameters of the proposed imaging procedure with the stored information of one or more prior performed cases 100. To avoid overly small result datasets 1002 being generated by the comparison, some variations of one or more parameters of the dose setting, number and duration of sequences and/or pauses could optionally be generated from the parameters of any matched prior performed cases 100 to increase the number of located/matched prior performed cases 100, if necessary. The software program/algorithm utilized within the thermal prediction system 200 can be or include any suitable matching algorithm, analysis engine, or machine learning or natural language process loaded onto the processing unit 201 in order to provide the comparison and/or matching in block 1000. The results of the matching in block 1000 include a dataset 1002 including a number of similar prior performed cases 102 out of the prior performed cases 100 that are determined to match the search parameters specified for the proposed imaging procedure and which can serve as initial models 102 for the proposed imaging procedure.

Figure 4:
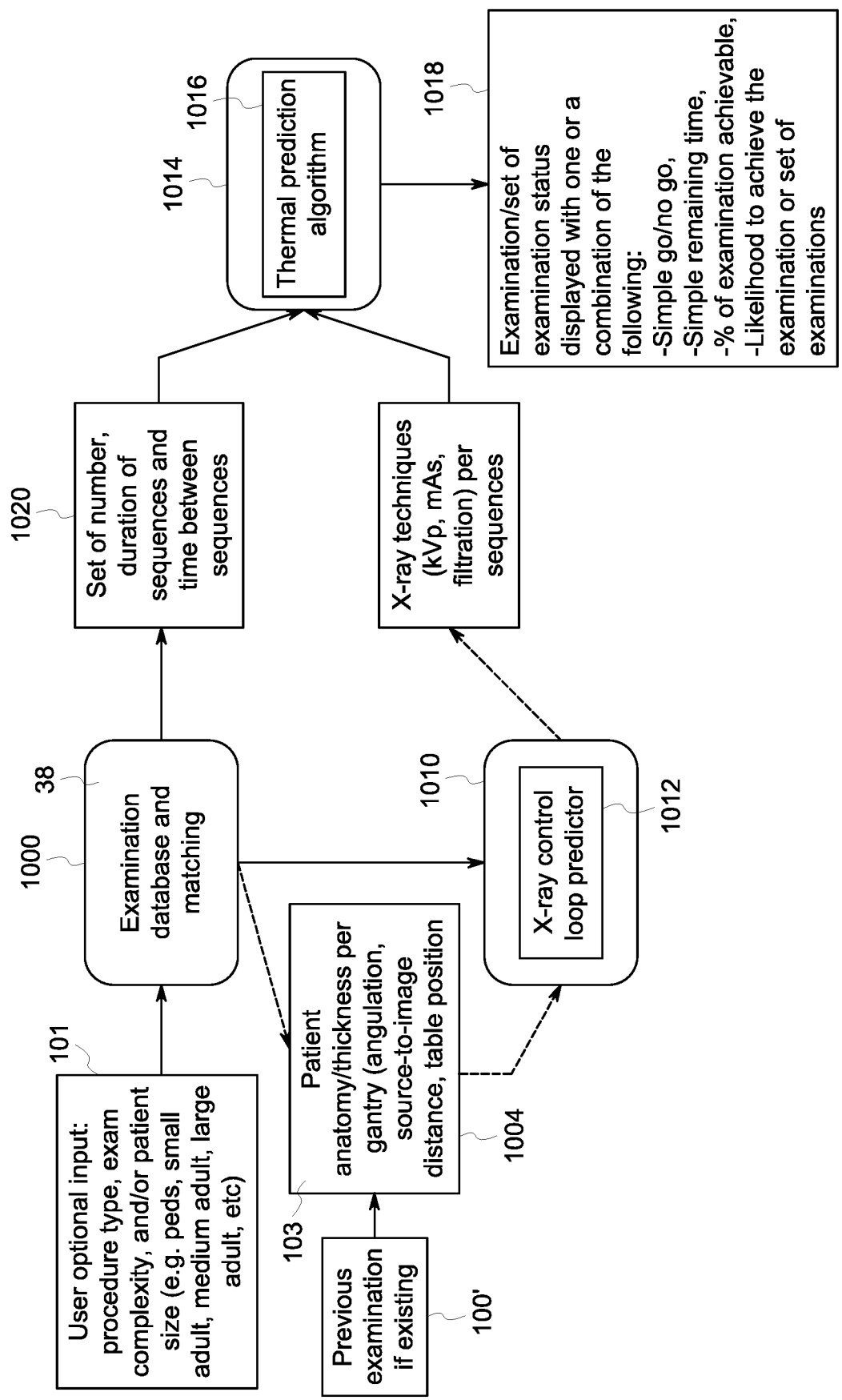
FIG. 4 is a flowchart of the operation of the thermal prediction system in accordance with another exemplary embodiment of the disclosure.

In one exemplary embodiment illustrated in FIGS. 3 and 4, the dataset 1002 of the similar cases/models 102 is further refined in block 1004, i.e., customized and augmented, utilizing additional input data 101 that is particular to the patient in order to obtain a dataset 1006 of refined models 108 that more closely approximate and/or predict what the actual steps and/or performance of the proposed imaging procedure will be. More specifically, the thermal prediction system 200 refines the search parameters employed by the system 200 in block 1000 and applies them to each of the similar prior performed cases/models 102 in the dataset

1002 in this process. This modification or customization performed in block 1004 employs data relating to the current morphology of the patient/patient data. In an exemplary embodiment, this current patient morphology data 103 is data contained in an electronic file for the patient or that is obtained by the system 200 through analysis of a current 3D scan from a 3D camera or a recent imaging scan of the patient, such as a CT scan. This patient data/information can be used by the thermal prediction system 200 in a variety of manners to customize the dataset 1002, such as by filtering the dataset 1002 to identify models 102 having acquisition angulations based on anatomical variations of the patient. However, though situations where filtering of the dataset 1002 based on patient shape data would be advantageous, in other implementations filtering of the dataset 1002 by the processor 201 would be based on the type of intervention and, after augmenting the dataset 1002 by adding variations to the number and duration of acquisitions and pauses, the augmented similar exam dataset 1006 would be personalized to better fit the patient, e.g. by adjusting angulation, as some angles are not attainable for larger patients due to collisions, in which case, the closest attainable angle would be selected using a 3D model of the patient and the imaging system. to identify individual similar models 102 in the dataset 1002 that match or best approximate the geometry in which the images are acquired in each of the proposed imaging procedure, such as the field of view, the orientation or angulation of the X-ray tube/beams, the source to image distance, and/or the table position/angle or location of the anatomy being imaged, among others. With these modifications to the search parameters for the similar cases 102 in dataset 1002 based on the current patient morphology, the system 200 eliminates or adds a number of the similar cases 102 and produces the augmented dataset 1006 of refined models 108, which more accurately approximate the predicted steps of the proposed imaging procedure to be performed. In the event that the utilization of the patient morphology data overly reduces the number of refined models 108 present in the dataset 1006 variations can be made to the morphology parameters to allow for the generation/location of additional refined models 108.

After production of the dataset 1006 of refined models 108, the thermal prediction system 200 proceeds to block 1010 and analyzes each of the refined models 108 using an X-ray control loop predictor 1012 that can be formed as part of the thermal prediction system 200 or that can be a part of the imaging system 10. The control loop predictor 1012 reviews each refined model 108 and adjusts various operational characteristics for the X-ray tube 14 in view of the information contained in each refined model 108, e.g, the patient morphology and/or the system geometry for the imaging, and the limitations of the X-ray tube 14. In particular, the control loop predictor 1012 can determine certain control parameters, including but not limited to, dose level, frame rate, image quality, kV, mA and ms, for the various steps of each refined model 108 in view of the patient morphology. This modification by the control loop predictor 1012 can be performed by any suitable control algorithm, including a suitable a neural network, regressions-based algorithm, or other computer or processor-controlled process similar to that disclosed in US Patent Application Publication NI. 2004/0125921, entitled Method To Determine The Optimal Parameters Of A Radiography Acquisition, the entirety of which is expressly incorporated herein by reference for all purposes, and translates the exam description from one or more of the refined models 108 into loading factors that the thermal model can take as inputs.

After making any refinements to the refined models 108 via the control loop predictor 1012, the dataset 1006 of the remaining refined models 108 can be analyzed in block 1014 by a thermal prediction model/algorithm 1016. In one exemplary embodiment, the thermal prediction algorithm 1016 forms a part of the thermal prediction system 200 and operates to analyze the various steps of each refined model 108 in dataset 1006, including the imaging sequences the associated operational parameters and the pauses between sequences, to determine if the refined model 108 can be performed in its entirety in view of the current HUA/operational conditions for the X-ray tube/source 14 as determined by the thermal prediction algorithm 1016 optionally using thermal data from sensing devices 202. Though any suitable method or process for modeling the thermal properties of an X-ray tube 14 for a proposed imaging procedure can be employed for the algorithm 1016, one example of a algorithm 1016 suitable for this purpose is disclosed in U.S. Pat. No. 6,377,657, entitled, Method And Load Calculator To Calculate The Temperature Distribution Of An Anode Of An X-ray Tube, the entirety of which is expressly incorporated herein by reference for all purposes. (The results of the analysis illustrate whether the likely case 1018 can be performed in its entirety or if the refined model 108 would trigger a derating of any imaging sequence steps in the refined model 108 or a protection, i.e., the prevention of the completion of the entire refined model 108.

The output from the analysis in block 1014 by the thermal prediction algorithm 1016 is provided to an indicator 1018 operably connected to the imaging system 10, such as connected to or forming a part of the monitor/display 42, and optionally to a remote computer system 400. The indicator 1018 can display a percentage of the refined models 108 that would not trigger a derating nor a thermal protection, if the refined model(s) 108 was to be initiated immediately. In addition to or as a separate embodiment for the information provided by the indicator 1018, as thermal conditions for the imaging system 10 are constantly changing as the system 10 cools when idle, e.g. in-between cases, the indicator 1018 could also display a cooling time needed for the imaging system 10 to reach a target percentage (e.g. 99% or 95%) regarding the probability of the completion of the entire analyzed refined model 108. Further, in combination with the other information provided via the indicator 1018, or as a separate embodiment, the indicator can also indicate the percentage of the steps of each refined model 108 that could be successfully performed prior to reaching a derating or, alternately or in addition to a thermal protection. In still another embodiment for the indicator 1018, the results of the analysis of the thermal prediction algorithm 1016 can be provided as one or more of a simple go/no go for the performance of the entire likely case 108, a simple remaining cooling time required for performance of the entire refined model(s) 108, a percentage of the refined model(s) 108 that can be successfully performed and/or a likelihood/probability/percentage of the refined model(s) 108 or dataset 1006 of refined model(s) 108 that can be successfully completed in their entirety.

With regard to the situation where the thermal prediction algorithm 1016 indicates that any predicted step for the refined model(s) 108 will trigger a derating or a protection, the thermal prediction system 200 can propose an adjustment or change to the step and/or refined model(s) 108, such as a change to the dose level or power level, in order to allow the performance of the entire proposed imaging procedure.

As an alternative embodiment for the operation of the thermal prediction system 200, in block 1002 the system 200 can determine whether any of the prior performed cases 100' have been conducted directly on the patient that is the subject of the proposed imaging procedure. If so, as shown in FIG. 4, the system 200 can utilize the particular prior performed case(s) 100 for the patient as the dataset 1002 of similar prior performed case(s)/initial models 102 output from block 1000. This particular prior performed case(s)/initial model 102 can then be directly analyzed by the thermal prediction algorithm 1016, or customized using any available patient morphology data, as done in block 1004, and analyzed/modified by the X-ray control loop predictor 1012 prior to analysis by the thermal prediction algorithm 1016.

In still another alternative exemplary embodiment to the matching performed in block 1000, for very reproducible and codified types of proposed imaging procedures or cases, e.g., a percutaneous coronary intervention, a standardized model 1020 can be built using the parameters of one or more prior performed cases 100 for the proposed imaging procedure by utilizing just a few parameters of the prior performed cases 100 for which a probabilistic distribution is known from experience. This "hand-crafted" or standardized model 1020 can be created in any suitable manner, such as by being based off of information contained within publications from medical societies, an analysis of a large sample of prior exams, or by a computer. This standardized model 1020 can then be directly analyzed by the thermal prediction algorithm 1016, or customized using any available patient morphology data, as done in block 1004, and analyzed/modified by the X-ray control loop predictor 1012 prior to analysis by the thermal prediction algorithm 1016.

In still another exemplary embodiment of the thermal prediction system 200, when the proposed imaging procedure is initiated after the results of the thermal prediction algorithm 1016 have been provide by the indicator 1018, refinements can be made by the thermal prediction system 200 to the set of refined models 108 in dataset 1006, such as by eliminating any refined models 108 that are shorter than the actual proposed imaging procedure or by adjusting operating parameters, such as the kV, mA, ms from an X-ray loop prediction model or system geometry (e.g. SID) or dose setting or fps actually selected for the in-process proposed imaging procedure. The new dataset 1006 of refined models 108 including these modifications can regularly be run through the thermal prediction algorithm 1016 and the indicator(s) 1018 updated accordingly during the performance of the proposed imaging procedure. In this step, Optionally, an alert can be raised when the projected likelihood to encounter a derating or tube protection reaches a certain threshold in run-time, where the system 200 can suggest user actions to reduce this likelihood, e.g., a reduction of the dose or power level.

In still a further exemplary embodiment of the thermal prediction system 200, the system 200 can be utilized to determine the feasibility of the performance of a number of proposed imaging procedure during an entire day. As the initial temperature/HUA for the X-ray tube 12 is known from the typical ambient temperature or from measurement of the surrounding cooling oil/water, the system 200 can access hospital scheduling software and the desired case planning for the day, including a list of cases as well as a starting time which are provided to the system 200 as the input 101, shown in FIG. 3. As the actual duration of each planned case is not accurately predictable, the cases are usually run one after the other with pauses limited to cleaning the room, a lunch break or change of team break. With estimations generated by the system 200 for the cleaning pause and based on the usage pattern of the system 10 in the database of cases filtered for a particular user/team, the thermal prediction system 200 can perform the prior described analysis to locate (block 1000), optionally customize (block 1004), and modify (block 1010) refined models 108 similar to each of the planned cases for the day and run these refined models 108 predicting the steps for each planned case through the thermal prediction algorithm 1016. The results of the analysis from the thermal prediction algorithm 1016 provided through the indicator 1018 can enable the operator to predict whether a derating or a thermal protection is likely to occur during any of the planned cases. The operator can then attempt to alter the steps of one or more of the planed cases to remove the derating or protection, or alternatively to reorder the planned cases to minimize the potential for exceeding the HUA for the X-ray tube 12 during the performance of the planned cases. In still another alternative embodiment, the thermal prediction system 200 can run all permutations of the cases for the day in any order with one or more estimated pauses for cleaning, lunch breaks and/or patterns if use(s) for a user or team. The system 200 can then output via the indicator 1018 a suggestion for the case order which is likely to minimize the risk of encountering a derating or tube protection.

Finally, it is also to be understood that the system 10 may include the necessary computer, electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor/processing unit/computer and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application(s)/algorithm(s) that adapts the computer/controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A method for predicting an outcome for performing a complete proposed X-ray imaging procedure on an object, the method comprising the steps of:
    a. providing an X-ray imaging system comprising:
        i. a X-ray source configured to emit radiation beams towards the object;
        ii. an X-ray detector movably aligned with the X-ray source to receive the radiation beams from the X-ray source and generate image data;
        iii. a controller operably connected to the X-ray source and the X-ray detector to control the movement and operation of the X-ray source and X-ray detector, the controller configured to receive and process image data from the X-ray detector;
        iv. a display operably connected to the controller for presenting information to a user;
        v. a user interface operably connected to the controller to enable user input to the controller; and
        vi. a thermal prediction system including a processing unit operably connected to the controller; and
        vii. an electronic storage device including data on a number of prior performed imaging procedures;
    b. inputting imaging procedure data to the thermal prediction system;
    c. matching the proposed imaging procedure data with one or more prior performed imaging procedures to create one or more models for the proposed imaging procedure; and
    d. performing a thermal prediction on the one or more models.

2. The method of claim 1, further comprising the steps of:
    a. developing a standardized model for the proposed imaging procedure from the one or more matched prior performed cases; and
    b. performing the thermal prediction on the standardized model.

3. The method of claim 1, wherein the step of matching the proposed imaging procedure data with one or more prior performed cases comprises locating one or more prior performed cases on the object.

4. The method of claim 1, further comprising the step of refining the one or more models by altering parameters of the one or more models to form one or more refined models.

5. The method of claim 1, further comprising the step of displaying an output of the thermal prediction.

6. The method of claim 4, wherein the step of refining the one or more models comprises altering the parameters for the one or more models in view of morphology data for the object to form the one or more refined models.

7. The method of claim 6, wherein the morphology data is a scan of the object.

8. The method of claim 5, wherein the output of the thermal prediction is a probability of completion of the proposed imaging procedure.

9. The method of claim 5, wherein the output of the thermal prediction is a time delay required to reach a specified probability limit for successful completion of the proposed imaging procedure.

10. The method of claim 5, wherein the output of the thermal prediction is a percentage of the one or more models with a successful completion.

11. A method for predicting an outcome for performing a complete proposed X-ray imaging procedure on an object, the method comprising the steps of:
    a. providing an X-ray imaging system comprising:
        i. a X-ray source configured to emit radiation beams towards the object
        ii. an X-ray detector movably aligned with the X-ray source to receive the radiation beams from the X-ray source and generate image data;
        iii. a controller operably connected to the X-ray source and the X-ray detector to control the movement and operation of the X-ray source and X-ray detector, the controller configured to receive and process image data from the X-ray detector;
        iv. a display operably connected to the controller for presenting information to a user;
        v. a user interface operably connected to the controller to enable user input to the controller; and
        vi. a thermal prediction system including a processing unit operably connected to the controller; and
        vii. an electronic storage device including data on a number of prior performed imaging procedures;
    b. inputting imaging procedure data to the thermal prediction system;
    c. matching the proposed imaging procedure data with one or more prior performed imaging procedures to create one or more models for the proposed imaging procedure; and
    d. performing a thermal prediction on the one or more models,
    wherein the step of performing the thermal prediction comprises:
        i. obtaining thermal data from one or more sensing devices operably connected to the X-ray source; and
        ii. analyzing the one or more models in comparison with thermal data using a thermal prediction algorithm within the processing unit.

12. An X-ray imaging system comprising:
    a. an X-ray source configured to emit radiation beams towards an object;
    b. an X-ray detector movably aligned with the X-ray source to receive the radiation beams from the X-ray source and generate image data;
    c. a controller operably connected to the X-ray source and the X-ray detector to control the movement and operation of the X-ray source and X-ray detector, the controller configured to receive and process image data from the X-ray detector;
    d. a display operably connected to the controller for presenting information to a user;
    e. a user interface operably connected to the controller to enable user input to the controller; and
    f. a thermal prediction system including a processing unit operably connected to the controller; and
    g. an electronic storage device including data on a number of prior performed imaging procedures, wherein the processing unit for the thermal prediction system is configured to match input proposed imaging procedure data with one or more prior performed imaging procedures to create one or more models for the proposed imaging procedure, and to perform a thermal prediction on the one or more models.

13. The X-ray imaging system of claim 12, wherein the processing unit for the thermal prediction system is configured to refine the one or more models by altering parameters of the one or more models to form one or more refined models.

14. The X-ray imaging system of claim 12 wherein the processing unit for the thermal prediction system is configured to perform the thermal prediction by analyzing the one or more models in comparison with thermal data obtained from one or more sensing devices operably connected to the X-ray source using a thermal prediction algorithm within the processing unit.

15. The X-ray imaging system of claim 12, wherein the processing unit for the thermal prediction system is configured to present an output of the thermal prediction on the display.

16. The X-ray imaging system of claim 13, wherein processing unit for the thermal prediction system is configured to alter parameters for the one or more models in view of morphology data for the object to form the one or more refined models.

17. The X-ray imaging system of claim 15 wherein the output of the thermal prediction is at least one of: a probability of completion of the proposed imaging procedure, a time delay required to reach a specified probability limit for successful completion of the proposed imaging procedure, and a percentage of the one or more models with a successful completion.

18. A thermal prediction system for an X-ray imaging system, the thermal prediction system comprising:
   a. a processing unit;
   b. a number of thermal sensing devices adapted to be disposed on an X-ray source for the X-ray imaging system, and configured to send thermal data to the processing unit; and
   c. an electronic storage device including data on a number of prior performed imaging procedures,
   wherein the processing unit for the thermal prediction system is configured to match proposed imaging procedure data with one or more prior performed imaging procedures to create one or more models for the proposed imaging procedure, and to perform a thermal prediction on the one or more models.

* * * * *